United States Patent [19]

Rorig et al.

[11] Patent Number: 4,650,874
[45] Date of Patent: Mar. 17, 1987

[54] N-(ARALKOXYBENZYL)-4(BENZHYDRYL) PIPERIDINES

[75] Inventors: Kurt J. Rorig; Chi-Dean Liang, both of Glenview; Robert W. Hamilton, Wilmette, all of Ill.

[73] Assignee: G. D. Searle & Co., Skokie, Ill.

[21] Appl. No.: 674,900

[22] Filed: Nov. 26, 1984

[51] Int. Cl.$^4$ .................. C07D 211/14; C07D 211/18
[52] U.S. Cl. .................................... 546/236; 546/237; 546/239; 514/317; 514/331
[58] Field of Search ...................... 546/236, 239, 237; 514/317, 331

[56] References Cited

U.S. PATENT DOCUMENTS

| 3,759,928 | 9/1973 | Zivkovic | 546/236 |
| 3,862,173 | 1/1975 | Carr et al. | 546/236 |
| 4,035,372 | 7/1977 | Deason et al. | 260/293.77 |
| 4,356,184 | 10/1982 | Deason et al. | 424/267 |

FOREIGN PATENT DOCUMENTS

| 748568 | 10/1970 | Belgium | 546/240 |
| 862769 | 1/1977 | Belgium | |
| 1542823 | 3/1979 | United Kingdom | |

OTHER PUBLICATIONS

Stedman's Medical Dictionary, 23rd edition (1977) p. 1433.
Abstract of Ja 0128740 (Oct. 1981) and of FR 2534580-A (Apr. 1984).

Primary Examiner—Norma S. Milestone
Attorney, Agent, or Firm—Stuart L. Melton

[57] ABSTRACT

The invention relates to compounds of the formula:

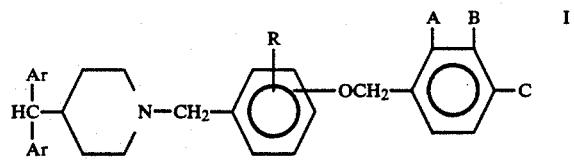

which are useful cardiovascular agents.

2 Claims, No Drawings

N-(ARALKOXYBENZYL)-4(BENZHYDRYL) PIPERIDINES

BACKGROUND OF THE INVENTION

The present invention provides novel compounds of formula I

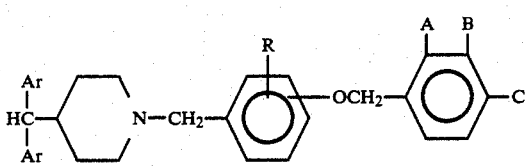

which are pharmacologically useful as cardiovascular agents. More specifically, the compounds of the present invention promote renal, coronary and peripheral vasodilation by the antagonism of calcium ions at arteriolar vessels. Thus, the compounds of the invention are useful generally as vasodilators, and specifically as calcium ion antagonists, antihypertensive agents, and anti-anginal agents, for example. The present invention also relates to novel pharmaceutical compositions comprising one or more of the active compounds of the invention in combination with suitable pharmaceutical carriers as well as methods of using such compounds and pharmaceutical compositions thereof in the treatment, prevention, or mitigation of cardiovascular diseases or conditions such as arrhythmias, angina-pectoris, hypertension, peripheral vascular disorders, etc. wherein abnormalities in the cellular or vascular handling of calcium ions is a causitive factor.

The compounds of formula I comprise (substituted)N-benzyl-4-(benzhydryl) piperidines wherein the substituents on the benzyl moiety thereof are aralkoxy derivatives in which the aryl moiety thereof may be further substituted.

Belgium Pat. No. 862769 discloses diphenyl methylene piperidine derivatives of the formula:

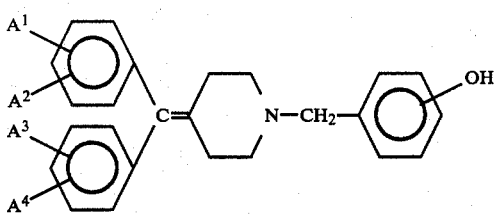

in which $A^1$-$A^4$ are H, halo, halomethyl, alkyl or alkoxy which are indicated to have utility as anti-convulsants and cardiovascular agents. The compounds disclosed in the foregoing Belgium patent are structurally unrelated to the compounds of the present invention by reason of the presence of optionally substituted diphenyl methylene (i.e., C=) attached to the piperidine ring and by the hydroxy substituent on the benzyl moiety rather than the aralkoxy or substitued aralkoxy moiety in accordance with the compounds of the present invention. The hydroxy derivatives disclosed in the foregoing Belgium patent are prepared by hydrolysis of a benzoate ester protected intermediate; however, only the hydroxy benzyl piperidine final products are associated with the indicated utility of the compounds.

U.S. Pat. No. 4035372 discloses 4[[4-(diphenylmethyl)-1-piperidinyl]methyl] benzenamines of the formula

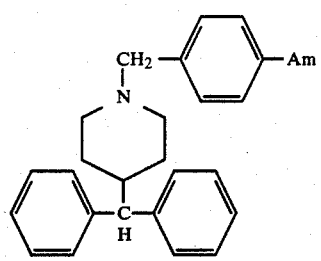

wherein Am represents an amino, alkanoylamino, alkylamino or dialkylamino radical and the vasodilating activity thereof. The compounds disclosed are all amino or substituted amino derivatives and, therefore, lack the aralkoxy moiety characteristic of the compounds of the present invention. U.S. Pat. No. 4356184 discloses 1-piperidinylmethyl benzenamines of the following formula:

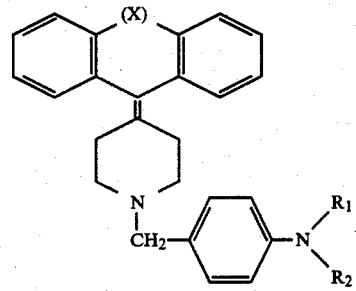

The foregoing compounds represent tricyclic ylidene piperidine derivatives rather than the diarylmethyl compounds of the present invention. Also, the substituent on the N-benzyl group is dialkyl amino rather than aralkoxy (e.g., benzyloxy). The compounds disclosed in the aforementioned U.S. Pat. No. 4356184 are indicated to be useful as anti-allergic and anti-hypertensive agents.

SUMMARY OF THE INVENTION

The present invention provides compounds of the general formula I:

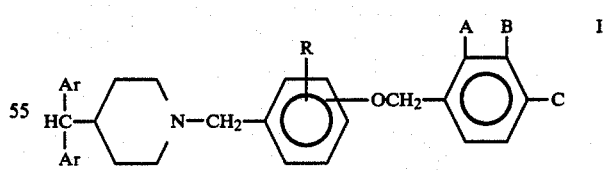

and pharmaceutically acceptable salts thereof wherein Ar are the same or different and represent phenyl or halogen substituted phenyl; R is selected from hydrogen, lower alkyl, lower alkoxy, alkoxycarbonyl, or alkylamino carbonyl; and A, B, and C are independently selected from hydrogen, halo, lower alkyl or lower alkoxy.

The compounds and pharmaceutical compositions thereof are useful in the cardiovascular methods of the invention.

DETAILED DESCRIPTION OF THE INVENTION

The compounds of the present invention comprise those of formula I:

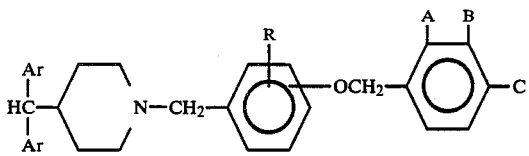

and the pharmaceutically acceptable salts thereof wherein Ar are the same or different and represent phenyl or halogen substituted phenyl; R is selected from hydrogen, lower alkyl, lower alkoxy, alkoxycarbonyl, alkylamino carbonyl; A, B, and C are independently selected from hydrogen, halo, lower alkyl, or lower alkoxy.

As used herein, the expressions "lower alkyl" and "lower alkoxy" are defined to include straight or branched carbon-carbon linkages of from about 1 to 6 carbon atoms. Representative alkyl moieties thereof include methyl, ethyl, propyl, butyl, pentyl, sec-butyl, etc. and the corresponding other isomeric forms thereof.

The expression "aryl" includes phenyl or napthyl and substituted derivatives thereof.

The term "halogen" includes bromine, chlorine, and fluorine with chlorine and fluorine being especially preferred.

The compounds herein may also be prepared as addition salt forms thereof and such forms are included in the present compound formulas. Typical of such "pharmaceutically acceptable salts" are those derived from non-toxic mineral or organic acids including, for example, hydrochloric, hydrobromic, hydroiodic, sulfuric, nitric, acetic, oxalic, maleic, succinic, and the like.

Exemplary of preferred halo substituted phenyl substituents corresponding to Ar are chloro- or fluoro-phenyl derivatives. Particularly preferred of these are those compounds wherein the halogen is fluoro and both Ar of the benzhydryl moiety are fluoro-phenyl and the fluoro substituent is at the 3-(meta) or 4-(para) position of the phenyl rings.

With respect to substituents A, B and C, especially preferred are alkyl or alkoxy (particularly, methyl or methoxy) and wherein two of A, B, or C are hydrogen and the other is methyl or methoxy in the 4-(para) position of the phenyl ring of the benzyloxy moiety.

When A, B, or C correspond to halo substituents, for use in the antihypertensive pharmaceutical compositions and methods of the present invention, chloro and fluoro are especially preferred. Most preferred are those compounds wherein the phenyl ring of the benzyloxy moiety is substituted by one or two chloro atoms, i.e., one of A, B, or C is hydrogen and chloro atoms are in the para position, ortho-para or meta-para positions.

Representative of especially preferred compounds in accordance with the present invention are those of formula II:

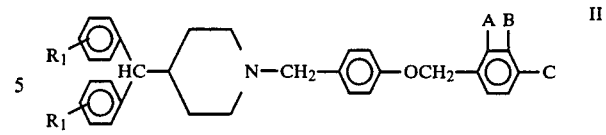

wherein
$R_1$ = H or F
$R_2$ = H or F
$R_1$ and $R_2$ = F in the 3- or 4-position relative to the —CH bond point.
A = H or Cl
B = H or Cl
C = Cl Another group of preferred compounds are those of formula III:

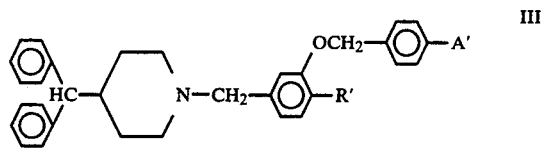

wherein
A' = H, Cl, or F
R' = lower alkyl or lower alkoxy.

Particularly preferred compounds of formula III are those wherein A' is chloro and R' is methoxy. The compounds of the invention are prepared according to the following general reaction scheme.

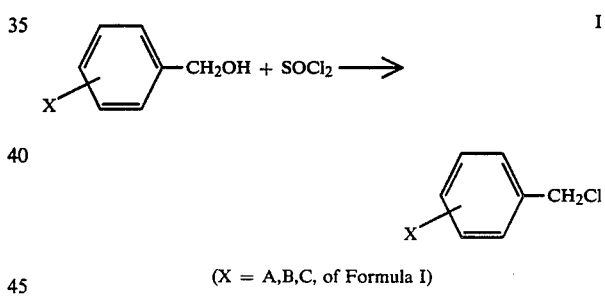

(X = A,B,C, of Formula I)

The benzyl alcohol derivative (10 mmole) in 20 ml. CH$_2$Cl$_2$ was cooled to 0° C. to which was added SOCl$_2$ (10 mmoles) in 5 ml CH$_2$Cl$_2$ dropwise during 0.5 hr. After 2 hours at 0° C. (while stirring) 20 ml of H$_2$O was added and the organic phase was separated. It was washed with H$_2$O (3×10ml), dried over MgSO$_4$, filtered and the solvent removed. The crude benzyl chloride was used for the next reaction without purification.

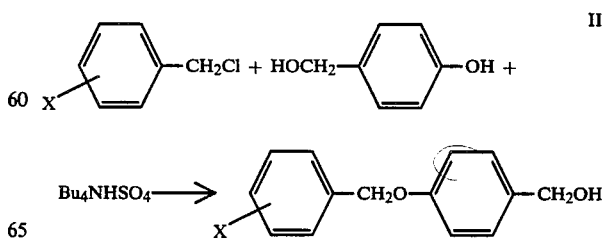

To crude benzyl chloride (10 mmole), p-hydroxy benzyl alcohol (10 mmole) and Bu$_4$NHSO$_4$ (10 mmole) in 20 ml CH$_2$Cl$_2$ was added 2N NaOH dropwise at room temperature. Stirring at room temperature for 2 hours was continued. 20 ml CH$_2$Cl$_2$ and 20 ml H$_2$O were added and the organic phase was separated and washed with H$_2$O (3×20 ml). The separated organic phase was dried and filtered and solvent removed. The benzyloxy benzyl alcohol derivative was purified by column chromatotography, or recrystalized from skellysolve B. NMR (CDCl$_3$) 4.56 (S, 2H), 4.98 (S, 2H), 6.75–7.0 (m. aromatic proton).

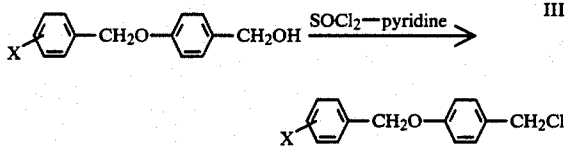
III

To the benzyloxy benzyl alcohol derivatives (10 mmole) in 40 ml CH$_2$Cl$_2$ was added 10 mmole of pyridine and cooled to 0° C. 10 mmole of SOCl$_2$ in 10 ml of CH$_2$Cl$_2$ was added dropwise over 0.5 hr. followed by stirring at 0° C. for 2 h. 10 ml of H$_2$O was added and the organic phase was separated. The organic layer was washed with H$_2$O (3×10 ml) and dried over K$_2$CO$_3$, filtered and solvent was separated. The corresponding benzyloxy benzyl chloride was used without purification.

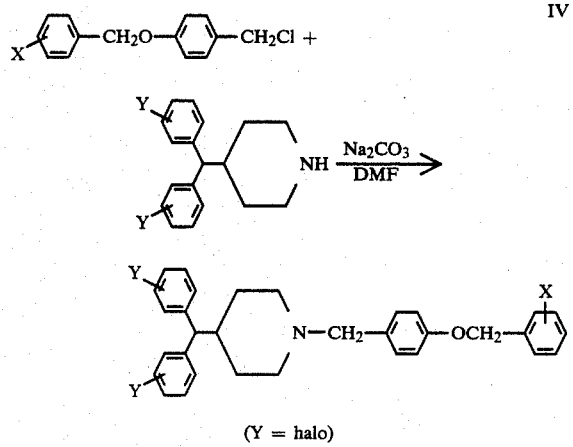
IV (Y = halo)

To the benzyloxy benzyl chloride from III in 30 ml DMF was added 20 mmole of K$_2$CO$_3$, 10 mmole of benzyhydryl piperidine and the mixture was heated to 80° C. followed by stirring at 80° C. overnight. The reaction mixture was cooled to room temperature and 90 ml of ether added followed by 20 ml of water. The organic phase was separated and washed with H$_2$O (3×20 ml) and dried over MgSO$_4$, filtered and solvent removed. The final product was purified by column chromatography.

The compounds of the present invention can be administered in such oral dosage forms as tablets, capsules, pills, powders, granules, elixers, or syrups. Likewise, they may also be administered intravascularly, intraperitoneally, subcutaneously, or intramuscularly using forms known to those of ordinary skill in the pharmaceutical arts. In general, the preferred form of administration is oral. An effective but non-toxic amount of the compound is employed in the treatment of hypertension or to promote calcium antagonism, coronary vasodilation, etc. with resultant cardiovascular improvement.

The dosage regimen utilizing the compounds of the present invention is selected in accordance with a variety of factors including the type, age, weight, sex, and medical condition of the patient; the severity of the condition to be ameliorated; the route of administration; and the particular compound employed or mixtures thereof. An ordinarily skilled physician can readily determine and prescribe the effective amount of the drug required to prevent, treat or arrest the progress of the condition. Dosages of the compounds of the present invention, when used for the indicated cardiovascular effects (e.g. hypotensive, anti-anginal, coronary dilation or calcium antagonist effect) will range between about 0.2 mg/kg/day to about 0.4 mg/kg/day. The foregoing dosage ranges on a weight basis correspond to a total daily dosage in the average adult patient of between about 15 mg/day to 30 mg/day. Advantageously, the compounds of the present invention may be administered in a single daily dose. Of course, should it be necessary or desirable, the total daily dosage may be administered in equal divided doses three or four times daily.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of this invention exhibit antihypertensive activity as determined in the unanesthetized spontaneously hypertensive rat (SHR) assay and/or exhibit calcium ion antagonism as demonstrated in isolated thoracic aorta segments from male spontaneously hypertensive rats. It should be observed that a selected compound may be inactive at a particular test dose in the SHR assay but be active in the calcium antagonist assay and contrariwise. Such compounds may be active at higher doses or by different administration routes or dosing regimens. Moreover, it should be noted that compounds active in the calcium antagonist assay, but inactive in the SHR assay at the same or lower dose, represent advantageous anti-anginal agents, renal or coronary arteriolar dilating agents, etc. consistent with the ultimate cardiovascular utility of the compounds of the present invention.

The test procedures employed to measure the antihypertensive and/or calcium antagonist activity of the compounds of the present invention are described below.

ANTI-HYPERTENSIVE ACTIVITY

Male, unanesthetized spontaneously hypertensive rats, 11 to 16 weeks old were used in this test procedure. The compounds to be tested were administered intragastrically at a dose of 50 mg/kg or intraarterially/intravenously at a dose of 10 mg/kg.

Initial mean arterial blood pressure was measured directly via a previously implanted arterial catheter immediately before administration of the test compound. Blood pressure readings were made at 1, 2, 3, and 4 hours following administration of the test compound. A compound was rated active if the mean post treatment blood pressure of treated rats was significantly different (p less than or equal to 0.05) than that of the control group concurrently administered placebo. Statistical comparisons were made using the paired Student's T test with two sided probability calculations.

The spontaneously hypertensive rat exhibits a genetically-linked hypertension that is similar in most respects to essential hypertension in man. Guanethidine, Apresoline, Aldomet, Clonidine, and Captopril are active in the foregoing hypertensive rat assay and are clinically useful antihypertensive agents.

CALCIUM ANTAGONISM IN VASCULAR SMOOTH MUSCLE

Isolated thoracic aorta segments from the male spontaneously hypertensive rat were utilized in this test procedure.

The excised aorta segment was mounted in a tissue bath containing modified Krebs solution. After depolarization of the tissue with potassium (100 mM), calcium, in cumulative concentrations of $1 \times 10^{-3}$M, $3.2 \times 10^{-3}$M, and $1 \times 10^{-2}$M was injected into the bath to produce vascular smooth muscle contraction. The developed tension (in grams) is measured and control dose-response values obtained. After one hour of incubation with a test compound at $1 \times 10^{-6}$M concentration, the same doses of calcium ions were repeated. The log dose-response curves of the control and after treatment were analyzed by linear regression. The pA2 value was calculated as a measure of calcium antagonism of the test compound. See Van Rossum, J. M., Arch. Int. Pharmacodyn, 143, 299–330, 1963. A compound was considered active as a vascular calcium antagonist if the pA2 is 6.0 or greater.

Calcium ions play an essential role in induction and maintenance of vascular smooth muscle contractility. In potassium depolarized vascular smooth muscle, calcium antagonists may block the entry of calcium ions into the cell or act by other mechanisms to inhibit the contractions induced by calcium ions. The inhibition of calcium ion - induced contraction of vascular smooth muscle is used to test compounds for vascular calcium antagonism. Cardiovascular diseases such as arrythmias, angina-pectoris, hypertension, and peripheral vascular disease may be casually related to abnormalities in cellular handling of calcium ions. Calcium antagonists/entry blockers have been proven to be of value in the treatment of the aforementioned cardiovascular diseases or conditions. Verapamil, Nifedipine, Diltiazem and other drugs are active in the foregoing test and have, likewise, been demonstrated to be clinically useful cardiovascular agents.

The compounds of the present invention are long-acting antihypertensive agents which advantageously have not been found to produce tachycardia, tachyphylaxis, or orthostatic hypotension and the avoidance or minimalization of such adverse side effects is clearly significant with respect to the ultimate usefulness of the present compounds as cardiovascular agents.

Reduction in arterial blood pressure is effected by decreasing total peripheral resistance as a result of arteriolar vasodilation produced by antagonism of calcium ions at the arterioles. The compounds of the present invention also block the uptake of calcium ions into cultured vascular smooth muscle cells and antagonize the binding of nitrendipine to the calcium receptor in cardiac membranes.

The following non-limiting examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

EXAMPLE 1

4-(diphenylmethyl)-1-[[4-(phenylmethoxy)phenyl]methyl]piperidine (SC 32724)

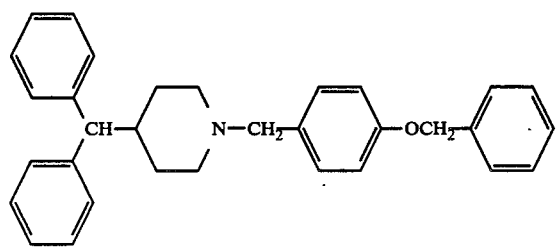

33.71 g (0.146 mole) of benzhydrylpiperidine, 41.66 g (0.175 mole) of p-benzyloxybenzylchloride, 24.20 g (0.175 mole) of 200 mesh $K_2CO_3$ and 400 ml of methylethyl ketone were stirred at 25° C. for 20 h. The solvent was removed under vacuum.

The resulting residue was partitioned in benzene and $H_2O$. The organic layer was separated, washed twice with $H_2O$, and dried over $K_2CO_3$ and concentrated. The residue was suspended in Skellysolve B, filtered and the insoluble matter discarded.

The filtrate was concentrated to approx. 500 ml and allowed to stand for 24 h at room temperature. The resultant precipitate was collected, and washed with Skellysolve B on a filter funnel and air dried to obtain 39.8 g (m.p. 113°–115°).

Calc. for $C_{32}H_{33}NO$, (M.W. 447.59): C, 85.86; H, 7.43; N, 3.13. Found: C, 86.16; H, 7.59; N, 3.25.

NMR (CDCl$_3$) ppm: 1.0–2.35 (m, 7H), 2.78 (d, 2H), 3.38 (s, 2H), 3.45 (d, 1H), 4.99 (s, 2H), 6.82 (d, 2H, J=9 Hz), 6.95–7.50 (m, 17H).

EXAMPLE 2 ethyl 2-[[4-(diphenylmethyl)-1-piperidinyl]methyl]-5-(phenylmethoxy)benzoate (SC40641)

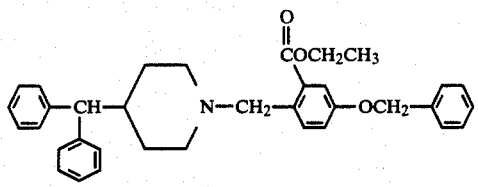

To the compound of Example 1 (7 g, 1.86 mmole) in 30 ml of benzene was added Pd(OAc)₂, 650 mg. (3 mmole) with stirring at room temperature for 72 h. 2 ml of ethyl alcohol was added to the reaction mixture and the mixture agitated with CO under pressure (10–25 psi.) for 3 h.

3 ml of Et₃N was added to neutralize the acetic acid and the black palladium metal was filtered. The organic material was obtained by the removal of the solvent in vacuo and purified by column chromatography. The title compound was obtained from EtOAc - toluene elution and was recrystalized from n-hexane to give 4 g, 56% product (m.p. 104°–106° C.).

Calc. for $C_{35}H_{37}NO_3$: C, 80.89, H, 7.18; N, 2.70. Found: C, 80.69; H, 7.41; N, 2.34.

NMR (CDCl₃) 1.3 (t. J=7 Hz, 3H), 1.7–2.2 (m, 2H), 2.5–3.0 (m, 2H), 3.46 (d, J=11 Hz, 1H), 3.67 (s, 2H), 4.27 (q, J=7 Hz, 2H), 5.0 (s, 2H), 6.5–7.5 (m, 18H).

EXAMPLE 3

4-(diphenylmethyl)-1-[[[4-methoxy-3-(phenylmethoxy)-phenyl]methyl]piperidine, ethanedioate (SC 39784)

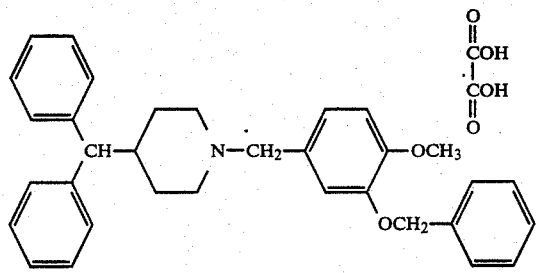

To 3-benzyloxy-4-methoxy benzaldehyde (2.4 g, 10 mmole) in 10 ml of ethanol was added NaBH₄ (120 mg, 3 mmole) at 10° C. for 10 min., then stirred for 0.5 h. at room temperature. After 1.5 h., the mixture was cooled to 0° C. and 10% acetic acid/90% H₂O was added until reaction ceased.

After removal of solvent, the mixture was extracted with 50 ml ethyl ether. The organic layer was washed with H₂O (3×10ml) and dried. Solvent was removed to obtain 2.25 g of material which was purified by thin layer chromatography (20% ethylacetate/toluene). To the resultant 3-benzyloxy-4-methoxy benzyl alcohol in 50 ml CH₂Cl₂ was added pyridine (0.8 g) and the mixture cooled to 0° C. 1.2 g of SOCl₂ in 10 ml of CH₂Cl₂ was added at 0° C. and stirred for 2 h. at 0° C. 10 ml of H₂O was added and the organic phase was separated, washed with H₂O (3×10 ml) and dried. The benzyl chloride thus prepared in 20 ml DMF was added to benzyhydryl piperidine (2.6 g) and 1.3 g. K₂CO₃ and heated at 80° C. for 17 h. After cooling to room temperature, the organic material was extracted with ethyl ether (40 ml).

The organic phase was washed (3×) and dried over Na₂SO₄ and filtered and solvent removed.

The oily substance was dissolved in 50 ml of ethyl ether and oxalic acid added until precipitate appeared. The precipitate was filtered to give the title product.

Calc. for $C_{33}H_{35}NO_2.C_2H_2O_4$ (M.W. 568): C, 74.05; H, 6.57; N, 2.47. Found: C, 73.78; H, 6.66; N, 2.39.

NMR(CDCl₃): 1.2–2.5 (m, 6H), 3.0–3.75 (m, 2H), 3.85 (S, 3H), 3.92 (d, 1H, J=8H$_z$), 5.15 (S, 2H), 6.70–7.5 (m, 20H).

EXAMPLE 4

2-[[4-(diphenylmethyl)-1-piperidinyl]methyl]-5-(phenylmethoxy)-N-(1,1-dimethylethyl) benzamide (SC 40703)

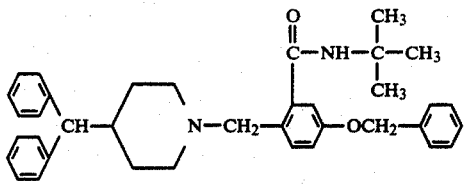

100 ml of Pd(OAc)₂ was added to the compound of Example 1 (1 g, 0.26 mmole) in 5 ml of benzene and was stirred at room temperature for 72 h. 0.3 ml of t-butylamine was added to the reaction mixture and then agitated under CO at 10–25 psi. for 3 h. The solid palladium metal was filtered and the organic material obtained after solvent removal was submitted for column chromatography. Elution with MeOH/CH₂Cl₂ solvent mixture yielded 0.7 g of the title compound which was recrystallized from Skellysolve B (m.p. 168°–172° C.).

Calc. for $C_{37}H_{42}N_2O_2$: C, 81.28; H, 7.74; N, 5.12. Found: C, 81.70, H, 7.85; N, 4.87.

NMR (CDCl₃) 1.42 (s, 9H), 1.7–2.25 (m, 2H), 2.5–3.0 (m, 2H), 3.48 (d, J=11 Hz, 1H), 3.33 (s, 2H), 5.05 (s, 2H), 6.75–7.25 (m, 18H).

Example 5

4-[[4-(diphenylmethyl)-1-piperidinyl]methyl]phenol (SC 32699)

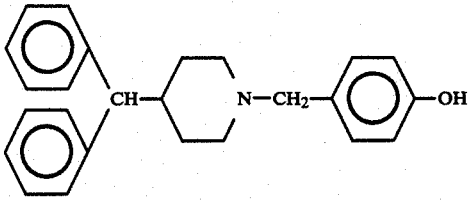

22.0 g (0.0492 mole) of the compound of Example 1 was dissolved in 1.1 L. of 95% ethanol with 2.81 ml (0.0492 mole) of glacial acetic acid and 4.4 g of 5% Pd/C was shaken in a Parr Shaker at room temperature at 2 psi. until the theoretical amount of hydrogen had been absorbed (5.5 h).

The reaction mixture was filtered and the solvent was removed from the filtrate by vacuum distillation.

The residue was partitioned in methylene chloride and sufficient 10% aqueous hydrochloric acid added to make the HCl salt. The mixture was shaken until a precipitate formed. The mixture was filtered and the residue recrystallized from methanol, m.p. 256–258° C.

Calc. for $C_{25}H_{27}NO\cdot HCl$: C, 76.22; A, 7.16; N, 3.56. Found: C, 75.86, H, 7.18; N, 3.44.

The free base was formed by suspending the hydrochloride salt in ether and water containing 1 mole of $K_2CO_3$ and shaking until homogeneous. The organic layer was separated, dried over anhy. $Na_2SO_4$ and concentrated. The precipitate obtained was dried in vacuo and recrystallized from benzene-Skellysolve B. m.p. 164°–165° C.

Calc. for: $C_{25}H_{27}NO$ (m.w. 357.50): C, 83.99, H, 7.61; N, 3.92. Found: C, 84.33; H, 7.61; N, 4.02.

NMR ($CDCl_3$): 1.0–2.35 (m, 7H), 2.92 (d, 2H), 3.38 (s, 2H), 3.54 (d, 1H), 6.48 and 6.98 (pair d, 4H, J=9 Hz), 7.18 (s, 10H).

The compounds set forth in Table I below were prepared according to the reaction scheme described previously in steps I through IV utilizing appropriate starting materials and conditions.

TABLE I

| Example No. | | Calc. For | Found | M.P. (°C.) | NMR (Significant Peaks) |
|---|---|---|---|---|---|
| 6. | 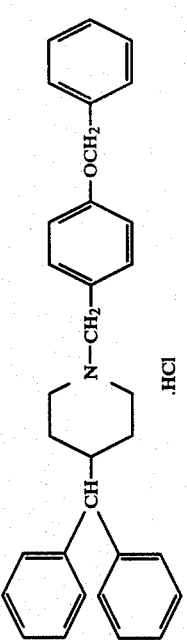<br>4-(diphenylmethyl)-1-[[4-(phenylmethoxy)phenyl]methyl] piperidine, hydrochloride (SC-39364) | C, 74.50<br>H, 7.72<br>N, 2.56 | 74.80<br>7.41<br>2.80 | 214-215 | 5.02 (s, 2H); 6.5-7.5 (m, 19H) |
| 7. | 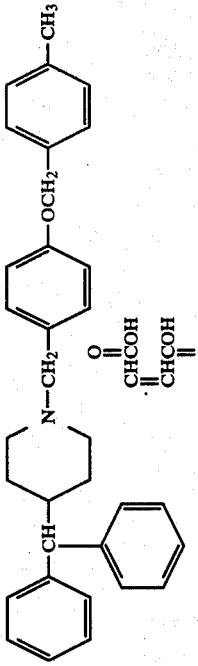<br>4-(diphenylmethyl)-1-[[4-((4-methylphenyl)methoxy)phenyl]methyl] piperidine, 2-butendioate (SC-39985A) | C, 76.92<br>H, 6.80<br>N, 2.42 | 76.58<br>6.44<br>2.25 | 183-184 | 1.5-1.75 (m, 4H); 2-2.75 (m, 1H)<br>2.32 (s, 3H); 3.25-3.6 (m, 3H)<br>6.75-7.5 (m, 18H) |
| 8. | 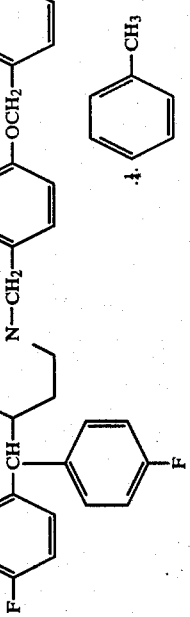<br>4-[bis(4-fluorophenyl)methyl]-1-[[4-[(4-methoxyphenyl) methoxy]phenyl]methyl]piperidine, cmpd. with methylbenzene (4:1) (SC-39659) | C, 77.77<br>H, 6.57<br>N, 2.61 | 77.92<br>6.61<br>2.83 | 152-153 | 1.0-3.0 (m, 8H); 3.4 (s, 2H)<br>3.5 (d, 1H, J = 8Hz);<br>3.78 (s, 3H); 4.92 (s, 2H)<br>6.6-7.4 (m, 16H) |

TABLE I-continued

| Example No. | | Calc. For | Found | M.P. (°C.) | NMR (Significant Peaks) |
|---|---|---|---|---|---|
| 9. | 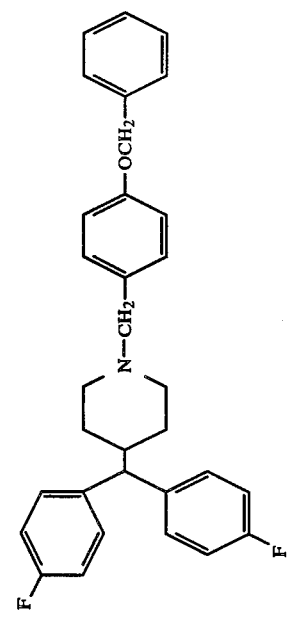 4-(diphenylmethyl)-1-[[4-[(4-methoxyphenyl)methoxy]phenyl]methyl]piperidine (SC-39424) | C, 82.98 H, 7.39 N, 2.93 | C, 82.9 H, 7.54 N, 2.77 | 122–123 | 3.4 (s, 2H); 3.5 (d, 1H, J = 8Hz); 3.78 (s, 3H); 4.92 (s, 2H); 6.5–7.5 (m, 18H) |
| 10. | 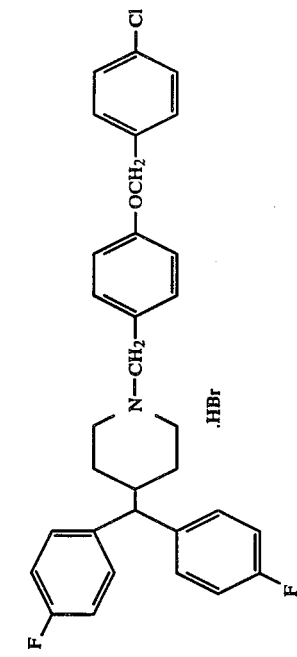 [bis(4-fluorophenyl)methyl]-1-[[4-[(phenylmethoxy)phenyl]methyl]piperidine (SC-39296) | C, 79.48 H, 6.46 N, 2.90 | C, 79.32 H, 6.63 N, 2.08 | 128–129 | 3.5 (d, 1H, J = 8Hz); (s, 2H); 5.01 (s, 2H); 6.5–7.5 (m, 17H) |
| 11. | 4-[bis(4-fluorophenyl)methyl]-1-[[4-[(4-chlorophenyl)methoxy]phenyl]methyl]piperidine, hydrobromide (SC-39613A) | C, 64.17 H, 5.22 N, 2.34 | C, 63.77 H, 5.27 N, 2.25 | 130–140 | 1–3.75 (m, 9H); 4.07 (s, 2H); 5.0 (s, 2H) |

TABLE I-continued

| Example No. | | Calc. For | Found | M.P. (°C.) | NMR (Significant Peaks) |
|---|---|---|---|---|---|
| 12. | 4-[bis(4-fluorophenyl)methyl]-1-[[4-[(2,4-dichlorophenyl) methoxy]phenyl]methyl]piperidine, hydrochloride (SC-39844) | C, 65.26<br>H, 5.13<br>N, 2.38 | 65.15<br>5.95<br>2.27 | 240–241 | 1.25–3.75 (m, 9H); 4.03 (s, 2H);<br>5.08 (s, 2H); 6.5–7.5 (m, 15H) |
| 13. | 4-[bis(3-fluorophenyl)methyl]-1-[[4-[(4-phenylmethoxy)phenyl] methyl]piperidine, cmpd. with benzene (2:1) (SC-39639) | C, 80.43<br>H, 6.56<br>N, 2.68 | 80.61<br>7.04<br>2.75 | 79–100 | 1.25 (s, 1H); 1.5–2.80 (m, 2H);<br>2.65 (s, 5H); 3.51 (d, 2H);<br>4.12 (s, 2H); 5.05 (s, 2H);<br>6.5–7.5 (m, 20H) |
| 14. | 1-[[4-[(4-chlorophenyl)methoxy]phenyl] methyl]-4-(diphenylmethyl)piperidine (SC-39584) | C, 79.73<br>H, 6.69<br>N, 2.91 | 79.96<br>6.76<br>2.80 | 125–126 | 4.9 (s, 2H); 3.4 (s, 2H)<br>3.44 (d, 1H, J = 8Hz) |

TABLE I-continued

| Example No. | Structure | Calc. For | Found | M.P. (°C.) | NMR (Significant Peaks) |
|---|---|---|---|---|---|
| 15. | 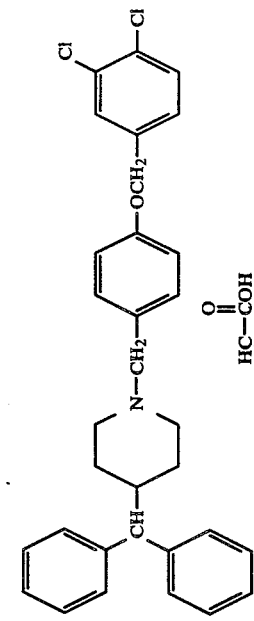<br>1-[[4-[(4-chlorophenyl)methoxy]phenyl]methyl]-4-(diphenylmethyl)piperidine, 2-butenedioate (SC-39584A) | C, 72.29<br>H, 6.07<br>N, 2.34 | 72.29<br>6.11<br>2.28 | 192–195 | 1–2 (m, 4H); 3.45 (m, 2H); 2.5 (m, 2H); 4.1 (s, 2H); 5.0 (s, 2H); 6.3 (s, 2H) |
| 16. | 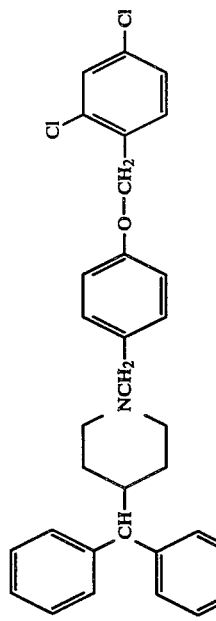<br>1-[[4-[(3,4-dichlorophenyl)methoxy]phenyl]methyl]-4-(diphenylmethyl)piperidine, 2-butenedioate (SC-39624A) | C, 68.35<br>H, 5.58<br>N, 2.21 | 68.07<br>5.57<br>2.98 | 153–155 | 1.0–3.0 (m, 8H); 3.5 (m, 1H); 4.98 (s, 2H); 6.3 (s, 2H); 6.75–7.25 (m, 12H) |
| 17. | 1-[[4-[(2,4-dichlorophenyl)methoxy]phenyl]methyl]-4-(diphenylmethyl)piperidine (SC-39758) | C, 74.41<br>H, 6.05<br>N, 2.71 | 74.41<br>6.00<br>2.67 | 118–120 | 1.0–2.5 (m, 6H); 2.5–3.0 (m, 2H); 3.4 (s, 2H); 3.48 (d, 1H, J = 8Hz); 5.08 (s, 2H); 6.25–7.5 (m, 17H) |

TABLE I-continued

| Example No. | | Calc. For | Found | M.P. (°C.) | NMR (Significant Peaks) |
|---|---|---|---|---|---|
| 18. | [structure: 4-(diphenylmethyl)-1-[[4-[(2-fluorophenyl)methoxy]phenyl]methyl]piperidine (SC-39676)] | C, 82.55<br>H, 6.93<br>N, 3.01 | C, 82.24<br>H, 7.01<br>N, 2.96 | 97–98 | 1.0–2.5 (m, 6H); 2.5–3.0 (m, 2H); 3.35 (s, 2H); 3.42 (d, 1H, J = 8Hz); 5.1 (s, 2H); 6.75-7.5 (m, 18H) |
| 19. | [structure: -[[3-[((4-chlorophenyl)methoxy]-4-methoxyphenyl]methyl]-4-diphenylmethyl)pipeidine (SC-42765)] | C, 77.40<br>H, 6.69<br>N, 2.74<br>Cl, 6.92 | C, 77.35<br>H, 6.66<br>N, 7.04<br>Cl, 7.04 | 97–98 | 1.0–2.2 (m, 6H), 2.5–3.0 (m, 2H); 3.3 (s, 2H), 3.4 (d, J = 11Hz, 1H), 3.76 (s, 3H), 5.05 (s, 2H), 6.7-7.4 (m, 17H) |
| 20. | [structure: 1-[[(4-cyclohexylmethoxy)phenyl]methyl]-4-(diphenylmethyl)piperidine (SC-40021)] | C, 84.72<br>H, 8.66<br>N, 3.09 | C, 84.59<br>H, 8.91<br>N, 2.99 | 118–119 | 0.75–2.20 (m, 20H); 2.76 (d, 2H J = 12Hz); 3.42 (s, 2H), 3.45 (d, J = 11Hz, 1H) |

TABLE I-continued
| Example No. | | Calc. For | Found | M.P. (°C.) | NMR (Significant Peaks) |
|---|---|---|---|---|---|
| 21. | 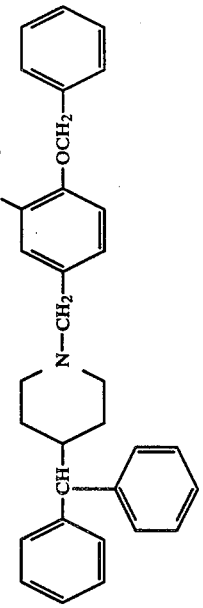<br>4-(diphenylmethyl)-1-[[3-methoxy-4-(diphenylmethoxy)phenyl]methyl]piperidine (SC-39695) | C, 82.98<br>H, 7.39<br>N, 2.93 | C, 82.83<br>H, 7.36<br>N, 2.90 | 109–111 | 1.0–2.4 (m, 6H), 2.6–3.1 (m, 2H), 3.39 (s, 2H), 3.82 (s, 3H), 3.5 (d, J = 11Hz, 1H), 5.08 (s, 2H), 6.8–7.6 (m, 18H) |

Certain of the preferred compounds of formula I were evaluated for activity in accordance with the test procedures described previously and the results are summarized in Table II.

TABLE II

| Compound Example No. | SHR -mm Hg @ 10 mg/kg intravenous | Threshold Dose mg/kg intravenous | pA2 (Ca++ Antagonism) | Oral Activity (Blood Pressure Lowering) |
|---|---|---|---|---|
| 1. | —[a] | — | 8.00 | active |
| 2. | inactive[b] | — | inactive | — |
| 3. | 79 | 0.3 | 7.59 | — |
| 4. | 29 | 0.3 | 6.73 | — |
| 5. | — | — | — | inactive |
| 6. | 88 | 0.3 | 7.97 | — |
| 7. | 56 | 1.0 | — | — |
| 8. | 50 | 1.0 | 7.74 | — |
| 9. | — | — | 7.38 | — |
| 10. | 67 | 0.3 | 7.57 | — |
| 11. | 107 | 0.3 | 8.06 | — |
| 12. | 79 | 0.1 | 7.52 | — |
| 13. | inactive | inactive | 7.89 | — |
| 14. | — | — | 7.41 | active |
| 15. | 89 | 1.0 | — | — |
| 16. | 81 | 0.3 | — | — |
| 17. | inactive | inactive | 7.39 | — |
| 18. | 65 | 0.3 | 7.15 | active |
| 19. | 75 | 1.0 | 6.34 | — |
| 20. | inactive | — | 7.35 | — |
| 21. | 18 | 0.1 | — | active |

[a](—) indicates no test conducted
[b]inactive at dose tested.

What is claimed is
1. A compound of the formula

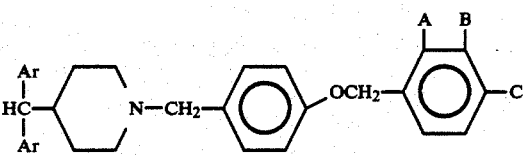

and the pharmaceutically acceptable salts thereof wherein
Ar=phenyl or m- or p-fluorophenyl
A=H or Cl
B=H or Cl
C=Cl
2. A compound according to claim 1 wherein said compound is of the formula

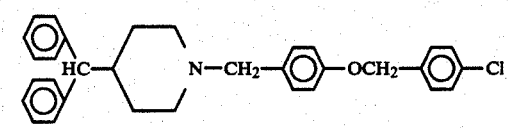

or a pharmaceutically acceptable salt thereof.

* * * * *